(12) United States Patent
Schanbacher

(10) Patent No.: US 11,554,108 B2
(45) Date of Patent: *Jan. 17, 2023

(54) METHODS AND COMPOSITIONS FOR TREATING CUTANEOUS FUNGAL INFECTIONS

(71) Applicant: Xeropedix, Inc., Boston, MA (US)

(72) Inventor: Carl F. Schanbacher, Boston, MA (US)

(73) Assignee: Xeropedix, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,082

(22) Filed: Apr. 8, 2019

(65) Prior Publication Data

US 2019/0231750 A1 Aug. 1, 2019

Related U.S. Application Data

(63) Continuation-in-part of application No. 15/683,146, filed on Aug. 22, 2017, now Pat. No. 10,501,668.

(60) Provisional application No. 62/380,787, filed on Aug. 29, 2016.

(51) Int. Cl.

| | | |
|---|---|---|
| *A61Q 19/00* | (2006.01) | |
| *A61P 31/00* | (2006.01) | |
| *A61P 17/00* | (2006.01) | |
| *A61K 8/00* | (2006.01) | |
| *A61K 9/08* | (2006.01) | |
| *A61K 9/70* | (2006.01) | |
| *A61K 31/4174* | (2006.01) | |
| *A61K 31/341* | (2006.01) | |
| *A61K 38/48* | (2006.01) | |
| *A61K 9/00* | (2006.01) | |
| *A61K 8/04* | (2006.01) | |
| *A61Q 15/00* | (2006.01) | |
| *A61K 8/26* | (2006.01) | |
| *A61K 8/28* | (2006.01) | |
| *A61K 31/137* | (2006.01) | |
| *A61K 8/02* | (2006.01) | |
| *A61P 31/10* | (2006.01) | |

(52) U.S. Cl.
CPC ........ *A61K 31/4174* (2013.01); *A61K 8/0208* (2013.01); *A61K 8/0229* (2013.01); *A61K 8/046* (2013.01); *A61K 8/26* (2013.01); *A61K 8/28* (2013.01); *A61K 9/0014* (2013.01); *A61K 9/08* (2013.01); *A61K 9/7007* (2013.01); *A61K 31/137* (2013.01); *A61K 31/341* (2013.01); *A61K 38/4893* (2013.01); *A61P 31/10* (2018.01); *A61Q 15/00* (2013.01)

(58) Field of Classification Search
CPC ...... A61Q 19/00; A61Q 15/00; A61Q 17/005; A61K 8/0208; A61K 47/10; A61K 2300/00; A61K 9/0014; A61K 2800/10; A61K 8/34; A61K 45/06; A61K 9/06; A61K 9/08; A61P 17/00; A61P 31/00
See application file for complete search history.

(56) References Cited

U.S. PATENT DOCUMENTS

| | | |
|---|---|---|
| 4,053,581 A | 10/1977 | Pader et al. |
| 4,083,954 A | 4/1978 | Tsuchiya et al. |
| 4,551,330 A | 11/1985 | Wagman et al. |
| 4,650,671 A | 3/1987 | Goldman |
| 4,822,603 A | 4/1989 | Faris et al. |
| 5,143,718 A | 9/1992 | Bar-Shalom |
| 5,468,473 A | 11/1995 | Mullen |
| 5,814,309 A | 9/1998 | Panitch |
| 2003/0215408 A1 | 11/2003 | Dees |
| 2005/0238672 A1 | 10/2005 | Nimni |
| 2006/0003649 A1 | 1/2006 | Runge et al. |
| 2007/0020220 A1* | 1/2007 | Osborne ............... A61K 8/64 424/70.14 |
| 2010/0056430 A1 | 3/2010 | Lester |
| 2012/0061267 A1* | 3/2012 | Villalobos ......... A61F 13/15203 206/223 |
| 2012/0114574 A1 | 5/2012 | Touitou |
| 2012/0321571 A1* | 12/2012 | Edelson ............... A61K 31/65 424/59 |

(Continued)

FOREIGN PATENT DOCUMENTS

| | | |
|---|---|---|
| EP | 2 191 828 A1 | 6/2010 |
| GB | 1024501 | 2/1963 |
| JP | S5824511 A | 2/1983 |

(Continued)

OTHER PUBLICATIONS

Matejuk et al. Peptide-based Antifungal Therapies against Emerging Infections. Mar. 2010. Drugs Future. 35(3):197. pp. 1-35. (Year: 2010).*

Alberti, I. et al., "Effect of Ethanol and Isopropyl Myristate on the Availability of Topical Terbinafine in Human Stratum Corneum, in Vivo", International Journal of Pharmaceutics, vol. 219, 2001; pp. 11-19.

Alsterholm, M. et al., "Antimicrobial Activity of Topical Skin Pharmaceuticals—An In vitro Study"; Acta Derm Venereol 2010; vol. 90: pp. 239-245.

(Continued)

*Primary Examiner* — Tracy Liu
(74) *Attorney, Agent, or Firm* — Cesari & McKenna, LLP

(57) ABSTRACT

The present invention relates to methods and compositions for the treatment of dermatophytic conditions such as tinea pedis. Such conditions can progress through multiple stages, such as fungal and bacterial stages, making effective treatment results difficult to achieve. The invention relates to a combined therapy effective for treatment of the condition that utilizes daily administration of a balanced combination of antifungals, antiperspirants and drying agents to achieve a beneficial therapeutic effect, irrespective of the stage of the disease upon commencement of the treatment.

14 Claims, No Drawings

(56) References Cited

U.S. PATENT DOCUMENTS

| | | | |
|---|---|---|---|
| 2013/0231379 A1* | 9/2013 | Koga | A61K 31/4178 514/397 |
| 2017/0020952 A1 | 1/2017 | Hruby et al. | |

FOREIGN PATENT DOCUMENTS

| | | | |
|---|---|---|---|
| JP | 2003335704 A | 11/2003 |
| JP | 2004351632 A | 12/2004 |
| JP | 200791643 A | 4/2007 |
| JP | 201627036 A | 2/2016 |
| JP | 2016510034 A | 4/2016 |
| RU | 2 567 036 C1 | 10/2015 |
| WO | 2007/039533 A2 | 4/2007 |
| WO | 2010/086732 A1 | 8/2010 |
| WO | 2015051805 A1 | 4/2015 |

OTHER PUBLICATIONS

Aluminum Starch Octenylsucinate, [online]. EWG's Skin Deep Cosmetics Database, 2016 [retrieved on Sep. 15, 2018]. Retrieved from V the lnternet:<URL:https://www.ewg.org/skindeep/ingredient/700326/ALU MIN U M_STARCH_ OCTENYLSU CCI NATE/#. WvM2KjbrtaQ >, 2016.

Aspres et al., "Predictive Testing for Irritancy and Allergenicity of Tea Tree Oil in Normal Human Subjects" Exogenoous Dermatology, 2003, vol. 2, pp. 258-261.

Bergstresser, P. R. et al., "Topical Terbinafine and Clotrimazole in Interdigital tinea Pedis: A Multicenter Comparison of Cure and Relapse rates with 1- and 4-week Treatment Regimens"; Journal of American Academy of Dermatology, vol. 28, No. 4; pp. 648-651.

Boboschko, I. et al., "Hyperhidrose als Risikofaktor der Tinea pedis", Der Hautarzt 2, Jan. 2005, pp. 151-154.

Brennan et al., Overview of Topical Therapy for Common Superficial Fungal Infections and The Role of New Topical Agents Journal of American Acedemy of Dermatology, Feb. 1997, pp. S3-S8.

Brown, M. et al., "Efficacy, Tolerability and Consumer Acceptability of Terbinafine Topical Spray versus Terbinafine Topical Solution: A Phase IIa, Randomised, Observer-Blind, Comparative Study" Adis Am J. Clin Dermatol, MedSpra Non-Inferiority Clinical Trial, Jun. 6, 2013, pp. 1-7.

Centers for Disease Control and Prevention, "Antibiotic Resistance Threats in the United States" 2013, pp. 1-14.

Ciftci, E. et al., "Mupirocin vs Terbinafine in Impetigo" Indian Journal of Pediatrics, vol. 69, Aug. 2002, pp. 679-682.

Crawford, F. et al., "Topical Treatments for Fungal Infections of the Skin and Nails of the Foot. (Review)" Cochrane Library—Cochrane Database of Reviews, 2016, pp. 1-161.

Cross, et al., "Human Skin Penetration of the Major Components of Australian Tea Tree Oil Applied in its Pure Form and as a 20% Solution in Vitro" European Journal of Pharmaceutics and Biopharmaceutics, vol. 69, 2008, pp. 214-222.

de Chauvin, M. F. et al., "Novel, Single-dose, Topical Treatment of Tinea Pedis using Terbinafine: Results of a Dose-finding Clinical Trial" The Authors, Journal Compilation 2007, Mycoses vol. 51, pp. 1-6.

Evans, E. G. V. et al., "Short-duration Therapy with Terbinafine 1% Cream in Dermatophyte Skin Infections", British Journal of Dermatology, 1994, vol. 130, pp. 83-87.

Federal Register, Proposed Rules, vol. 47, No. 56, Mar. 23, 1982, pp. 12541-12544.

Field, L. A. et al., "Tinea Pedis in Athletes", International Journal of Dermatology, 2008, vol. 47, pp. 485-492.

FM Tolnaftate 1% Spray (Jock) Powder, (2016), Perrigo Company, Safety Data Sheet, pp. 1-5, 2016.

Glaser et al., "Topical Glycopyrronium Tosylate for the Treatment of Primary Axillary Hyperhidrosis: Results from the ATMOS-1 and ATMOS-2 Phase 3 Randomized Controlled Trials", J Am Acad Dermatol, vol. 80, No. 1, Jan. 2019, pp. 128-138.e2.

GlaxoSmithKline Consumer Heathcare Holdings (US) LLC, Lamisil$^{AT}$ ® Terinafine Hydrochloride Cream Package Information and Directions, 2007, pp. 1-4.

Glogau, "Topically Applied Botulinum Toxin Type A for the Treatment of Primary Axillary Hyperhidrosis: Results of a Randomized, Blinded, Vehicle-Controlled Study" American Society for Dermatologic Surgery, Inc., 2007, vol. 33; pp. S76-S80.

Griffin et al., "An Agar Dilution Method for the Determination of the Minimum Inhibitory Concentration of Essential Oils" (Link: http://dx.doi.org/10.1080/10412905.2000.9699509), Journal of Essential Oil Research, vol. 12, No. 2, pp. 249-255.

Gupta A.K. et al., "An Overview of Topical Antifungal Therapy in Dermatomycoses A North American Perspective" Sunnybrook Health Science Center, and the University of Toronto, May 1998, vol. 55 No. 5, pp. 645-674.

Gupta, A. K. et al., "Update in Antifungal Therapy of Dermatophytosis" Mycopathologia, 2008 vol. 166, pp. 353-367.

Hill, et al., "An Investigation of the Pharmacokinetics of Topical Terbinafine (Lamisil) 1% Cream", University of Wales College of Medicine, Apr. 12, 1992 vol. 127, pp. 396-400.

Husni et al., "Effect of Extraction Methods on Antifungal Activity of Sea Cucumber (Stichopus japonicus)" Agrithech, vol. 34, No. 1 Feb. 2014, pp. 1-7.

International Searching Authority, International Search Report for International Application No. PCT/US2017/047971, dated Dec. 15, 2017, pp. 1-8.

James, I. G. et al., "Short-duration Topical Treatment of Tinea Pedis using Terbinafine Emulsion Gel: Results of a Dose-ranging Clinical Trial" Journal of Dermatological Treatment, Informa Healthcare, 2007, vol. 18, pp. 163-168.

Katz et al "Topical Antifungal Agents" Current Problems in Dermato, Mosby, vol. 12, No. 5, XP005466380, ISSN: 1040-0486, DOI: 10.1016/S1040-0486(00}80004-6, Tables 1 and 3, Sep. 2000 (Sep. 2000), pp. 226-229.

Koca et al., "İnterdijital Tip Tinea Pedis'te Klotrimazol ve Alüminyum Hidroksiklorid Kombinasyon Tedavisinin, Klotrimazol Tedavisi İle Karşilaşt1rtlmas1" O.N.Ü. Tip Dergisi, 2001, vol. 18(3), pp. 192-197, including partial translation.

Korting, H. C. et al., "Comparable Efficacy and Safety of Various Topical Formulations of Terbinafine in Tinea Pedis Irrespective of the Treatment Regimen: Results of a Meta-Analysis", Am J Clin Dermatol 2007, vol. 8(6), pp. 357-364.

Leyden, J. J. et al., "Aluminum Chloride in the Treatment of Symptomatic Athlete's Foot" Arch Dermatol—vol. 111, Aug. 1975, pp. 1004-1010.

Leyden, J. L., "Tinea Pedis Pathophysiology and Treatment" Journal of the American Academy of Dermatology, Sep. 1994, vol. 31, Issue 3, Part 2, pp. S31-S33.

Nolting, S. et al., "Clinical Relevance of the Antibacterial Activity of Terbinafine: A Contralateral Comparison between 1% Terbinafine Cream and 0-1% Gentamicin Sulphate Cream in Pyoderma", British Journal of Dermatology, 1992, vol. 126, Supplement 39, pp. 56-60.

Pranteda, G. et al., "Pitted Keratolysis, Erythromycin, and Hyperhidrosis" Dermatologic Therapy, vol. 27, 2014, pp. 101-104.

Rand, S., "Overview: The Treatment of Dermatophytosis", J Am Acad Dermatol, vol. 43, No. 5, Nov. 2000, vol. 43, pp. S104-S112.

Savin R. C., "Treatment of Chronic Tinea Pedis (Athlete's Foot Type) with Topical Terbinafine" J Am Acad Dermatol, vol. 23, No. 4, Part 2, Oct. 1990, vol. 23, pp. 786-789.

Schmook, et al., "Comparison of Human Skin or Epidermis Models with Human and Animal Skin in In-Vitro Percutaneous Absorption" International Journal of Pharmaceutics, vol. 215, 2001, pp. 51-56.

Seo, et al., "In Vitro Skin Absorption Tests of Three Types of Parabens using a Franz Diffusion Cell" Journal of Exposure Science and Environmental Epidemiology, 2016, pp. 1-6.

SIGMA, Product Information for Polymyxin B Sulfate, Jul. 7, 1997, pp. 1-2.

Soni et al., "Evaluation of the Health Aspects of Methyl Paraben: A Review of The Published Literature" Food and Chemical Toxicology vol. 40, 2002, pp. 1335-1373.

Soni et al., "Safety Assessment of Esters of P-Hydroxybenzoic Acid (Parabens)" Food and Chemical Toxicology, vol. 43, 2005, pp. 985-1015.

(56) References Cited

OTHER PUBLICATIONS

Syed et al., "Treatment of Toenail Onychomycosis with 2% Butenafine and 5% Melaleuca Alternifolia (Tea Tree) Oil in Cream" Tropical Medicine and International Health, vol. 4, No. 4, Apr. 1999, pp. 284-287.
Tong, et al., "Tea Tree Oil in the Treatment of Tinea Pedis" Australas J. Dermatol, 1992, vol. 33, pp. 145-149.
Walling, H. W., "Primary Hyperhidrosis Increases the Risk of Cutaneous Infection: A Case-control Study of 387 Patients" J Am Acad Dermatol, vol. 61, No. 2, pp. 242-246.
Weiss et al., "Solubility of Antibiotics in Twenty-four Solvents: Use in Analysis" Antibiotics and Chemotherapy vol. 7, No. 7, Jul. 1957, pp. 374-377.
Whitton et al., "The Thickness of the Epidermis" British Journal of Dermatology, 1973, vol. 89, pp. 467-476.
Anonymous: "Foot Powder Spray", XP055773106, Database GNPD [Online] MINTEL; Jul. 1, 2009 (Jul. 1, 2009) Database accession No. 1128168.
Anonymous: "Grande Powder Spray", XP055773118, Database GNPD [Online] MINTEL; Jan. 18, 2010 (Jan. 18, 2010), Database accession No. 1327323.
Anonymous: "Film Forming Solution", XP055773121, Database GNPD [Online] MINTEL; Mar. 5, 2008 (Mar. 5, 2008), Database accession No. 872445.
Notification of Reasons for Rejection issued in Japanese Patent Application No. 2019-531863 dated Aug. 2, 2022.

\* cited by examiner

METHODS AND COMPOSITIONS FOR TREATING CUTANEOUS FUNGAL INFECTIONS

RELATED APPLICATIONS

This application is a continuation in part application of U.S. Ser. No. 15/683,416, filed Aug. 22, 2017. This application also claims benefit to U.S. Provisional Patent Application Ser. No. 62/380,787, filed Aug. 29, 2016, the contents of both of which are incorporated herein by reference in their entireties.

FIELD OF THE INVENTION

The present invention generally relates to compositions and methods for treatment of cutaneous fungal infections including tinea pedis, tinea corporis, and tinea cruris.

BACKGROUND

Until the 1940s, there were few treatments of any kind for tinea pedis (athlete's foot). Those treatments available were generally nonspecific antifungals, caustic agents that damaged the skin rather than targeted treatments inhibiting fungi. Spurred by the prevalence of dermatophytoses among military personnel during the wars of the mid-twentieth century, the search for truly effective treatments began. Azole antifungals were first synthesized in the late 1960s, and over the next two decades, research and development focused on this class of treatments, representing a major breakthrough in the targeted treatment of fungal infections. Further progress was made with the development of potent fungicidal allylamines in the 1990s. Today, one such allylamine, terbinafine, remains the most potent treatment for tinea infections. Terbinafine is the most effective topical agent against tinea pedis (Crawford & Hollis, Cochrane Database of Systematic Reviews 2007, Issue 3. Art. No.: CD001434). Unlike fungistats, which require up to four weeks of application, terbinafine is effective in a shorter course of treatment. Current labeling guidelines for terbinafine cream call for twice-daily application for 1-2 weeks (Lamisil AT® Drug Facts, (GlaxoSmithKline Consumer Healthcare Holdings, 2017).

By comparison, antiperspirant treatment for tinea pedis has received relatively little academic attention. The only notable example of an antiperspirant treatment for tinea pedis comes from a 1975 study by Leyden & Kligman (Arch Dermatol, Vol. 111, p. 1004, August, 1975). They found that a 30% aluminum chloride solution was effective at reducing unpleasant symptoms of tinea pedis. However, this treatment did not resolve the infection entirely; instead, it transformed the macerated, malodorous form of tinea pedis associated with bacterial co-infection (sometimes called dermatophytosis complex) back into the dry, scaly type that indicates a purely fungal infection (dermatophytosis simplex). Because of the focus on the development of antifungals that promised to treat the underlying cause of tinea pedis, there has been little further research on the use of antiperspirants in the treatment of tinea pedis. In 2001, Koca et al. (O. M. Ü. Tip Dergisi Cult: 18 No. 3, p. 192, 2001) conducted a study on a combination antiperspirant-antifungal therapy. Patients were instructed to apply cream containing clotrimazole (a fungistatic azole antifungal) in the morning, and aluminum chlorohydrate cream in the evening. The researchers found no benefit from the addition of an antiperspirant compared to antifungal therapy alone.

Dees (U.S. Pat. No. 7,201,914) describes combining an antiperspirant with an antimicrobial for the treatment of acne. Dees does not describe any standard topical antifungal agents as examples of antimicrobial agents. Lester (U.S. Pat. Publication No. 2010/0056430) describes reducing foot odor using antibacterial antibiotic agents with other ingredients such as terbinafine and aluminum chloride, but Lester did not combine his materials with an alcohol drying agent or use them in combination for treatment of infections such as dermatophytosis. Furthermore, the unnecessary use of antibiotics creates risks, both individual (such as allergic reaction) and societal (such as antibiotic resistance), which this invention seeks to avoid. Villalobos (U.S. Pat. Publication 2012/0061267) describes using a terbinafine wipe with alcohol. Villalobos does not use an antibacterial agent (such as an antibiotic) or an antiperspirant compound and failed to demonstrate efficacy.

What is needed is an effective therapy that can be applied for the efficient treatment of dermatophytic infections irrespective of the stage of the infection. What is also needed is a composition that resolves bacterial co-infection while avoiding problems associated with antibiotic use.

SUMMARY OF THE INVENTION

A problem in the prior art was that previous compositions overlooked the positive impact antiperspirants and other anti-sweating agents can have on treating symptomatic fungal infections. Additionally, the benefit of combining a suitable antiperspirant with a suitable antifungal and the resulting synergism that provides an accelerated therapeutic effect were also unrecognized. Moreover, the significance of the proper treatment vehicle for patient compliance and treatment success cannot be understated. Another important feature is the elimination of the buildup of bacteriological immunity to antibiotics by avoiding the use of antibiotics.

The present invention is directed to compositions and methods comprising an antifungal agent and an antiperspirant to treat tinea pedis and other fungal infections such as tinea cruris. The antifungal agent and the antiperspirant complement each other and offer a significantly better treatment than either would on its own.

One preferred embodiment of the present invention comprises the combination of an antifungal agent, an antiperspirant, a solvent, and a vehicle for solution delivery. The antiperspirant (aluminum chloride hexahydrate) and solvent (aqueous ethanol) work synergistically: the antiperspirant reduces sweat and the solvent dehydrates the skin, creating a dry environment that makes it harder for fungi and bacteria to grow. This activity complements the antifungal's action against the fungi as well as the antibacterial properties of the antiperspirant and the solvent.

The compositions of the present invention are more effective in treating tinea pedis than previous compositions, and overcome deficiencies of prior conventional methods used to treat tinea pedis.

In one aspect, the invention includes a method for treating a dermatophytic infection. The method can include the steps of topically applying an antifungal, topically applying an antiperspirant comprising an aluminum salt, topically applying a solvent vehicle comprising an alcohol, where the antifungal, the antiperspirant and the solvent vehicle are all applied during a single administration event, and repeating the administration event not more than about daily.

Embodiments of the invention include using a fungicidal antifungal, and the fungicide can be an allylamine. A suitable fungicide is terbinafine, or a pharmaceutically acceptable salt thereof. In some embodiments the antifungal is a fungicide that includes at least one of amorolfin, butenafine, naftifine, terbinafine or tolnaftate, or pharmaceutically acceptable salts thereof. Preferably, the method is repeated until the infection is resolved, and resolution of the infection can be determined using the KOH (potassium hydroxide) microscopy test for the presence of a fungus.

In some embodiments the antiperspirant of the method is or comprises aluminum chloride hexahydrate. The solvent vehicle can either include or be ethanol (ethyl alcohol). Duration of the treatment can range between one and four weeks, for example depending upon treatment efficacy. Daily administrations are preferred, as this can prevent overdrying of the treated area. Other antifungals can be used with the invention. As such, the method can include the use of the following antifungals: an azole, including at least one of clotrimazole, ketoconazole, fluconazole, flutrimazole, itraconazole, bifonazole, butoconazole, econazole, fenticonazole, isoconazole, luliconazole, miconazole, omoconazole, oxiconazole, sertaconazole, sulconazole, tioconazole, tiabendazole, croconazole, chlormidazole, neticonazole, terconazole, posaconazole, voriconazole, albaconazole, isavuconazole, eberconazole, or efinaconazole; or a polyene, including at least one of amphotericin B, nystatin, hamycin, and natamycin; or at least one of nystatin, natamycin, hachimycin, pecilocin, mepartricin, pyrrolnitrin, griseofluvin, bromochlorosalicylanilide, methylrosaniline, tribromometacresol, undecylenic acid, polynoxylin, 2-(4-chlorophenoxy)-ethanol, chlorphenesin, ticlatone, sulbentine, ethyl para-hydroxybenzoate, haloprogin, selenium sulfide, ciclopirox, dimazole, flucytosine, benzalkonium chloride, benzoyl peroxide, benzoic acid, salicylic acid, tannic acid, boric acid, gentian violet, chlorhexidine, cetylpyridinium chloride, tolciclate, sodium thiosulfate, potassium iodide, tea tree oil, citronella oil, lemongrass oil, garlic, vinegar, tavaborole, abafungin, an echinocandin (caspofungin, micafungin, and anidulafungin), nikkomycin, a pradimicin, or a benanomycin; or pharmaceutically acceptable salts thereof. Of these, amorolfine, clioquinol, nystatin, natamycin, hachimycin, pyrrolnitrin, griseofulvin, haloprogin, ciclopirox, and tolciclate are specific antifungals useful in the treatment of tinea pedis and related dermatophytoses. More preferred agents include amorolfine, ciclopirox, and tolciclate, whose efficacy is similar to that of azole specific antifungals. Nonspecific antifungals, such as Whitfield's ointment, s paint, gentian violet, tea tree oil, and aluminum chloride, are largely ineffective in the treatment of dermatophytoses and are not preferred in this invention.

Another aspect of the invention relates to a composition for treatment of a dermatophytic infection, the composition comprising an antifungal, an antiperspirant drying agent that includes an aluminum salt, and a cream-free solvent vehicle comprising an alcohol for delivery of the antifungal and the drying agent. The antifungal, preferably, is a fungicide, which can be terbinafine, or a pharmaceutically acceptable salt thereof.

Compositions of the invention also include a fungicide that includes at least one of amorolfin, butenafine, naftifine, terbinafine or tolnaftate, or pharmaceutically acceptable salts thereof. The composition can be administered via a wipe, or a "towelette," e.g., from a sealed, disposable, tear-away package or packet. One disposable wipe packet can be opened and used on a daily basis to effectively treat the condition, and a second packet used on the second day, etc., until the infection is resolved. This treatment duration may only need to be for about a week seven packets/administrations), or for some situations two to four weeks of treatment a daily basis) may be required.

Compositions of the invention include terbinafine present in an amount of between 0.5 and 10% of the composition by weight. The aluminum salt (e.g., aluminum chloride hexahydrate) can be present in an amount of not more than about 30% by weight (of the composition). In some embodiments, the aluminum salt amount is reduced to between about 15 and 20% by weight. A preferred antiperspirant is aluminum chloride hexahydrate ($AlCl_3.6H_2O$).

Yet another aspect of the invention includes a solution for treating a dermatophytic infection that can be produced by the following process. Terbinafine (or pharmaceutically acceptable salts thereof) is added to a liquid solvent solution that either is or includes ethanol. A measured amount of aluminum chloride, such as crushed $AlCl_3.6H_2O$, is added to the solution, then the solution is made up, e.g., with additional ethanol, to an aluminum chloride concentration of about 200 gm/liter, and a terbinafine concentration of about 10 gm/liter of the solution. Preferable, the terbinafine and the AlCl3 are thoroughly dissolved to create a uniform solution. The solution can be added to a wipe for eventual treatment of a patient, such as for a dermatophytic condition. The wipe can be stored in a packet, as described above.

Embodiments include producing the solution using terbinafine that is provided as a powder, and the amount added can be not in excess of about 100 gm/liter. Embodiments also include having AlCl3 present in an amount of not more than about 300 gm/liter of the solution.

Another aspect of the invention includes a kit embodying the invention. The kit can include an article or a container that includes an antiperspirant comprising an aluminum salt dissolvable in an alcohol solvent, such as a solvent including an alcohol (such as ethanol), in an amount of about 200 gm/liter, a fungicide dissolvable in the solution, and the alcohol solvent. The fungicide and the antiperspirant can be dissolved in the alcohol solvent to form a solution, and the container be used to house the article.

In embodiments of the kit the fungicide includes at least one of amorolfin, butenafine, naftifine, terbinafine or tolnaftate, or pharmaceutically acceptable salts thereof. The kit can also include an applicator, such as a wipe and/or a roller ball. In some embodiments the kit includes at least 7 wipes fir administration of the solution, and each wipe can be packaged separately, e.g., for daily use. The kit can also include a calendar and/or an instruction set, the calendar for tracking a daily administration of a treatment of how the materials of the kit are being used.

An aspect of the invention includes an antibiotic-free composition effective in treating a dermatophytic infection. Preferably, the composition is antibacterial-free as well. The composition includes a specific antifungal, as described herein, an anti-sweating agent, and one or more excipients, e.g., to assist with topical application of the composition. The specific antifungal should be present in an amount sufficient to effectively treat the dermatophytic infection. The anti-sweating agent should include at least one of an antiperspirant, an anticholinergic, or a neuromodulator.

Embodiments of the invention include the specific antifungal being one of an allylamine, a benzylamine, an azole, a thiocarbomate, ciclopirox, or amorolfine. In other embodiments the specific antifungal includes at least one of luliconazole, lanoconazole, efinaconazole, sertaconazole, an echinocandin, or tavaborole. The specific antifungal can also include at least one of a polyene, clioquinol, griseofulvin, haloprogin, pyrrolnitrin, or fluconazole.

The anti-sweating agent of the compound can be an antiperspirant active that includes at least one of an aluminum halide, an aluminum chlorohydrate, an aluminum hydroxyhalide, a zirconyl oxyhalide, a zirconyl hyroxyhalide, a zinc halide, an aluminum-zirconium salt, or complexes or adducts thereof with glycols or neutral amino acids. In other embodiments, the antiperspirant active of the anti-sweating agent can include at least one of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrate poylethylene glycol, aluminum sesquichlorohydrate propylene glycol, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, or aluminum zirconium trichlorohydrex gly.

When the anti-sweating agent of the composition is an anticholinergic, the anticholinergic can include glycopyrronium tosylate. When the anti-sweating agent of the composition is a neuromodulator, the neuromodulator can include onabotulinum toxin A.

Excipients of the composition can be a liquid, and the composition can then be in the form of a solution. In such embodiments the excipient solution can include an alcohol, such as ethanol. In other embodiments, the excipient can include at least one of a solvent, solid or semisolid carrier, diluent, bulking agent, propellant, foaming agent, film-forming agent, emollient, humectant, thickening agent, delivery enhancer, surfactant, buffering agent, stabilizer, preservative, absorbent, anti-static agent, fragrance, or colorant.

Another aspect of the invention is a method for antibiotic-free treatment of a dermatophytic infection. The antibiotic-free treatment can also be antibacterial-free. The method can include the steps of topically applying one or more specific antifungals present in an amount sufficient to effectively treat the dermatophytic infection, which are described below. One or more anti-sweating compounds are also applied topically, and the anti-sweating compound can include at least one of an antiperspirant, an anticholinergic, or a neuromodulator. Also topically applied is one or more excipients, to assist with the topical application. Preferably, the antifungal, the anti-sweating compound and the excipients are all applied during a single administration event, such that an efficacious result can be achieved by administrations that are applied on a daily basis, or even somewhat less frequently. The applying can be in different forms, including the form of a solution, a spray or a wipe.

Embodiments of the invention include the specific antifungal being one of an allylamine, a benzylamine, an azole, a thiocarbomate, ciclopirox, or amorolfine. In other embodiments the specific antifungal includes at least one of luliconazole, lanoconazole, efinaconazole, sertaconazole, an echinocandin, or tavaborole. The specific antifungal can also include at least one of a polyene, clioquinol, griseofulvin, haloprogin, pyrrolnitrin, or fluconazole.

In preferred embodiments, the method includes application of the specific antifungal such that a topical antifungal skin concentration of greater than or equal to the MIC of the antifungal results, thereby achieving a therapeutically effective result. Moreover, in preferred embodiments the specific antifungal is applied in a concentration sufficient to result in the topical antifungal skin concentration of the specific antifungal, 24 hours after application, to be equal to or greater than the MIC of the specific antifungal.

The anti-sweating agent of the method can be an antiperspirant active that includes at least one of an aluminum halide, an aluminum chlorohydrate, an aluminum hydroxyhalide, a zirconyl oxyhalide, a zirconyl hyroxyhalide, a zinc halide, an aluminum-zirconium salt, or complexes or adducts thereof with glycols or neutral amino acids. In other embodiments, the antiperspirant active of the anti-sweating agent used in the method can include at least one of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrate poylethylene glycol, aluminum sesquichlorohydrate propylene glycol, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, or aluminum zirconium trichlorohydrex gly.

When the anti-sweating agent of the method is an anticholinergic, the anticholinergic can include glycopyrronium tosylate. When the anti-sweating agent of the method is a neuromodulator, the neuromodulator can include onabotulinum toxin A.

In preferred embodiments, efficacious results of the method are achieved by applications of treatments for between one and four weeks, preferably at a frequency of not more than one administration event per day.

Another aspect of the invention includes a product composition produced by the following process. The composition for treatment of a dermatophytic infection is produced by the process of adding a specific antifungal to an excipient to create a mixture, then adding a measured amount of anti-sweating agent to the mixture. Next, additional excipient is added, if required, to establish a concentration of the specific antifungal agent sufficient to effectively treat the dermatophytic infection, such as to be able to achieve or exceed a suitably MIC after topical application. A uniform dispersion is established in the mixture that includes the specific antifungal, the anti-sweating compound and the excipient, by mixing, if necessary.

In some embodiments the composition of the mixture is distributed on a wipe for treatment of a dermatophytic condition of a patient, e.g., by topical application.

Embodiments of the mixture include the specific antifungal being one of an allylamine, a benzylamine, an azole, a thiocarbomate, ciclopirox, or amorolfine. In other embodiments the specific antifungal includes at least one of luliconazole, lanoconazole, efinaconazole, sertaconazole, an echinocandin, or tavaborole. The specific antifungal can also include at least one of a polyene, clioquinol, griseofulvin, haloprogin, pyrrolnitrin, or fluconazole.

The anti-sweating agent of the mixture can be an antiperspirant active that includes at least one of an aluminum halide, an aluminum chlorohydrate, an aluminum hydroxyhalide, a zirconyl oxyhalide, a zirconyl hyroxyhalide, a zinc halide, an aluminum-zirconium salt, or complexes or adducts thereof with glycols or neutral amino acids. In other embodiments, the antiperspirant active of the anti sweating agent can include at least one of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrate poylethylene glycol, aluminum sesquichlorohydrate propylene glycol, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, or aluminum zirconium trichlorohydrex gly.

When the anti-sweating agent of the mixture is an anticholinergic, the anticholinergic can include glycopyrronium tosylate. When the anti-sweating agent of the mixture is a neuromodulator, the neuromodulator can include onabotulinum toxin A.

In some embodiments, the excipient of the mixture includes an alcohol, such as ethanol.

Another aspect of the invention is a kit for the treatment of a dermatophytic condition. The kit includes an article. The article comprises one or more anti-sweating agents that includes at least one of an antiperspirant, an anticholinergic, or a neuromodulator. The kit also includes one or more specific antifungals present in an amount sufficient to effectively treat the dermatophytic infection, e.g., by enabling achievement of a topical specific antifungal concentration that is at least as great as, or greater than the MIC of the specific antifungal, preferably lasting even for as long as 24 hours or more after the topical application. The kit also includes one or more excipients to assist with the topical application of the composition that includes the specific antifungal and the anti-sweating agent. Preferably, the kit also includes a storage container for housing the at least one article.

Embodiments of the kit embodiment of the invention include the specific antifungal being one of an allylamine, a benzylamine, an azole, a thiocarbomate, ciclopirox, or amorolfine. In other embodiments the specific antifungal includes at least one of luliconazole, lanoconazole, efinaconazole, sertaconazole, an echinocandin, or tavaborole. The specific antifungal can also include at least one of a polyene, clioquinol, griseofulvin, haloprogin, pyrrolnitrin, or fluconazole.

The anti-sweating agent of the kit embodiment of the invention can be an antiperspirant active that includes at least one of an aluminum halide, an aluminum chlorohydrate, an aluminum hydroxyhalide, a zirconyl oxyhalide, a zirconyl hyroxyhalide, a zinc halide, an aluminum-zirconium salt, or complexes or adducts thereof with glycols or neutral amino acids. In other embodiments, the antiperspirant active of the anti-sweating agent can include at least one of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrate poylethylene glycol, aluminum sesquichlorohydrate propylene glycol, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, or aluminum zirconium trichlorohydrex gly.

When the anti-sweating agent of the kit embodiment of the invention is an anticholinergic, the anticholinergic can include glycopyrronium tosylate. When the anti-sweating agent is a neuromodulator, the neuromodulator can include onabotulinum toxin A.

In some embodiments, the kit further includes an applicator, the applicator including at least one of a wipe, push stick, spray or foam nozzle, aerosol container and nozzle, or roller ball.

DETAILED DESCRIPTION

Although antifungals have proven to be effective in terms of their ability to eliminate fungi, their clinical effectiveness in the treatment of tinea pedis is not impressive. Interdigital tinea pedis is, in many cases, not solely a fungal infection, and is therefore harder for antifungals alone to address. Fungal hyphae permeate the stratum corneum, weakening it and thus weakening the skin's defenses against further infection. Fungi also produce penicillin- and streptomycin-like substances. In this environment, penicillin-resistant bacteria proliferate, producing proteolytic substances, breaking down the tissue of the interdigital skin, resulting in maceration and leukokeratosis. These bacteria also produce sulfur compounds, which are potent natural antifungal agents. In these cases, the bacterial co-infection can actually eliminate the primary fungal infection; however, because the stratum corneum of the interspace has been weakened and a bacterial infection has taken root, the bacterial infection persists in the fungi's absence, preventing the stratum corneum from healing. In this stage of the disease, antifungal treatment alone is of limited effect, because the bacterial infection has become the primary issue.

These cases of tinea pedis may be significantly underrepresented in clinical trials. Because the bacteria have a natural antifungal effect, severe cases of tinea pedis that have reached the complex co-infection stage often give negative results on potassium hydroxide and culture tests, which are used to identify fungal infections. It is estimated that fungi are recovered in as little as one third of symptomatic interspaces (Leyden, J Am Acad Dermatol, Vol. 31, Issue 3, Part 2, 1994, p. S31). However, clinical trials to test the efficacy of antifungal drugs, which were common in the second half of the twentieth century, almost always required confirmation of fungal infection with both tests. This meant that tinea pedis patients whose disease had progressed to the point of bacterial superinfection would be underrepresented in these studies, because the severity of the infection resulted in the inability to confirm the presence of fungi in the test. Thus, studies that focused on antifungal efficacy likely overestimated the clinical effectiveness of the drugs, because a significant portion of tinea pedis patients were not included, and these patients suffered from a particularly unpleasant form of tinea pedis that antifungals would be unlikely to treat effectively.

Antifungals and antiperspirants are two effective and complementary weapons against tinea pedis and other dermatophytic infections. Antifungals are designed to eliminate fungi, either through destruction of the organisms (fungicide) or through preventing further fungal growth (fungistasis), allowing the skin to shed fungi with time. An antiperspirant can complement the action of an antifungal in two ways: by drying the skin and by killing bacteria. Antiperspirants can dry the skin in two ways: firstly, by precipitating plugs that obstruct sweat glands, preventing moisture from reaching the skin, and secondly, by acting as astringent agents, causing tissue to contract, which diminishes the skin's capacity to hold water and narrows the pores. Both fungi and bacteria thrive in wet environments like the foot (particularly the interdigital spaces), so the benefit of reduced moisture is significant. Indeed, epidemiologists have found that occlusive footwear is one of the most significant risk factors for tinea pedis, because it traps heat and moisture around the foot, providing an ideal environment for microbial growth.

The second beneficial aspect of aluminum-based antiperspirants is their antibacterial activity. Aluminum-based antiperspirants have been shown to have some in vitro as well as in vivo antibacterial effects at very high concentrations, indicating possible successful antibacterial action independent of the potent antimicrobial effect of drying the skin. This mild antibacterial effect may serve to supplement the drying effect; however, we believe that the drying effect is the primary mechanism that makes this treatment effective against tinea pedis. For example, in their study of aluminum salts as treatments for tinea pedis, Leyden & Kligman found that aluminum chlorohydrate, a more potent antibacterial agent but ineffective astringent, was less effective than aluminum chloride, which is less antibacterial but more astringent, indicating that moisture reduction rather than antibacterial activity is the primary mechanism through which antiperspirants alleviate the symptoms of tinea pedis.

The discovery that antiperspirants (and anti-sweating agents more broadly) can resolve the bacterial co-infection that distinguished complex tinea pedis is significant because of the increasing threat of antibiotic resistance (AR) due to overuse of antibiotic agents, and the subsequent desire for treatments that can resolve bacterial infections without using these agents. In AR, the overuse of antibiotic drugs leads to bacteria developing strains that resist the drugs, rendering the once-potent drugs ineffective. One famous example of AR is methicillin-resistant *Staphylococcus aureus* (MRSA), a resistant strain of the common *S. aureus* bacterium which has spread widely caused outbreaks and deaths in a variety of settings. In 2013, the CDC estimated that 2,000,000 illnesses and 23,000 deaths could be attributed to AR. With the threat of AR, physicians are likely to prefer a treatment that can resolve bacterial infections without the risk of AR from using antibiotics; for this reason, the finding that anti-sweating agents alone can resolve bacterial co-infection is very significant.

A further concern with antibiotic use is the possibility of allergic response. Allergic responses to topical antibiotics are common, ranging from a mild rash to life-threatening anaphylaxis. It is usually unknown whether a patient will have an allergic reaction to a particular antibiotic agent; because of these unpredictable and potentially severe side effects, physicians are hesitant to use antibiotics unless absolutely necessary. Thus, the antibiotic-free nature of this invention is beneficial, allowing physicians to confidently treat complex cases of dermatophytosis with fungal and bacterial involvement without exposing patients to the risks involved in antibiotic use.

Recent research has raised the possibility that the role of perspiration in tinea pedis and other dermatophytoses may be even more significant than previously understood. Several studies have found a link between plantar hyperhidrosis (excessive sweating of the feet) and tinea pedis. Researchers have generally hypothesized a causal link in one direction, i.e., those with preexisting hyperhidrosis are at greater risk for developing tinea pedis. However, recent research into pitted keratolysis, a bacterial infection of the foot, strongly suggests that hyperhidrosis is triggered by the infection, rather than vice versa (Pranteda et al., Dermatologic Therapy, Vol. 27, p.101, 2014). The authors theorize that the skin's inflammatory response to the infection prompts increased function of the sweat glands. It seems possible that a similar dynamic is at play in dermatophytoses. This model would indicate a vicious cycle, in which infection increases sweating, and this excess moisture creates conditions for the infection to become entrenched and intensify. If such a dynamic does take place, it would reinforce the role of antiperspirants in the successful treatment of tinea pedis, emphasizing the significance of the moist environment in the development of the infection.

The present invention is directed to compositions comprising an antifungal agent, an antiperspirant (or other anti-sweating agent), and an excipient vehicle to treat tinea pedis and other fungal infections such as tinea cruris. The antifungal agent and the antiperspirant complement each other and offer a significantly better treatment than either can provide alone. The antiperspirant complements the action of the antifungal in two ways: by drying the skin and killing bacteria. However, care must be taken to prevent overdrying of the skin during treatment, which can cause its own set of problems. The invention is intended to reduce excess moisture due to sweating, but if applied too frequently, it can cause the skin to dry out, which exacerbates some of the symptoms of tinea pedis, including erythema and desquamation. Furthermore, excessive dryness may prevent the skin from healing once the infection has been resolved, leaving the skin vulnerable to new infection once treatment stops. Administration of the drying agent not more than once daily appears to be particularly effective, as detailed below. The excipients comprising the vehicle can complement the activity of the active ingredients. Because of the antibacterial properties of the antiperspirant (and of some vehicles), the compositions of the present invention offer advantages over treating tinea pedis using antifungals alone, because many cases of tinea pedis involve a bacterial co-infection. This invention is also advantageous against fungal infections, because the drying effect of the antiperspirant (and, in some compositions, an alcohol-based vehicle) is inimical to fungal growth. Proper selection of an antifungal (e.g., a fungicide), an antiperspirant, and excipients which can form a drying solvent vehicle can result in a composition that is effective for the treatment of dermatophytic conditions regardless of the stage of the infection.

Antifungal Component

Antifungals are drugs that selectively eliminate fungal pathogens with minimum toxicity to the host. Extant antifungal therapies for tinea pedis can come in topical or systemic form. Systemic treatment is associated with a risk of hepatotoxicity; therefore, topical treatment is usually preferred for its safety profile, with systemic treatment pursued in cases where topical treatment is ineffective. Typical drug regimens are usually between 1-4 weeks. Different classes of specific antifungals target specific functions of the fungal cells.

Antifungals can be divided into nonspecific antifungals and specific antifungals (Katz, Current Problems in Dermatology, Vol, 12, p. 226, 2000). Nonspecific antifungals are those that do not directly inhibit or kill fungi; specific antifungals are those whose mechanism of action directly targets the growth, reproduction or viability of the fungi. Nonspecific antifungals are less effective, because they rely on destruction of the entire skin, removing the fungi with it. Specific antifungals are able to interfere in particular stages of fungal growth without damaging the surrounding skin.

One way to understand the differential efficacy of nonspecific and specific antifungals relates to differences in their minimum inhibitory concentrations (MICs) against *Trichophyton fungi*, the primary causative agents of tinea pedis and related dermatophytoses, compared to the bioavailability of those antifungals in the human stratum corneum. A compound's MIC is a measurement of its ability to inhibit the growth of a specified microbe. If an antifungal's MIC against *Trichophyton* spp. is 1 µg/ml, it will prevent the fungus's growth if the antifungal is present at a concentration at or above 1 µg/ml. Thus, a lower MIC indicates greater antifungal potency. This MIC can be compared with the concentration of the compound in the skin to estimate whether the antifungal will actively inhibit fungal growth in the skin (i.e., whether it possesses a specific action spectrum in vivo). This is an imperfect comparison, as MIC calculated in laboratory growth plates may not equate directly to the environment of the skin, and calculations of antifungal retention in the skin vary widely from study to study. But in general, if an antifungal's skin concentration is orders of magnitude lower than its MIC against Trichophyton fungi, it is reasonable to assume that the antifungal will not function as a specific antifungal (i.e., by inhibiting fungal growth), whereas if its concentration in the skin is orders of magnitude above its MIC, it will likely act as a specific antifungal (i.e., by inhibiting the growth of or killing the fungi). For example, Hill et al. find that 24 hours after application of 1% terbinafine cream, the concentration of terbinafine in the stratum corneum is approximately 148 µg/ml (British Journal of Dermatology, Vol. 127, p. 396, 1992). FIG. 4 indicates a stratum corneum concentration of 37 ng/cm$^2$ 24 hours after a single application; the authors indicate that with the depth of their skin surface biopsy, 1 ng/cm$^2$=4 µg/ml, so 37 ng/cm$^2$ equals a concentration of 148 µg/ml. The authors report that the minimum fungicidal concentration of terbinafine against *T. rubrum* as 0.003 µg/ml. The minimum fungicidal concentration is a strengthened form of the minimum inhibitory concentration; at the MFC, the antifungal kills a fungus rather than merely inhibiting its growth. Therefore, after 24 hours, terbinafine is present in the stratum corneum at a concentration of 148 µg/ml, whereas a concentration of 0.003 µg/ml would be sufficient to kill the fungus. The ability to maintain a concentration significantly higher than the minimum concentration required to inhibit the growth of dermatophytes indicates that terbinafine is indeed a specific antifungal.

In general, most specific antifungals have an MIC against *Trichophyton* species significantly less than 100 µg/ml. More effective specific antifungals have a concentration less than 1 µg/ml, and the most effective specific antifungals (such as terbinafine or butenafine) have concentrations less than 0.1 µg/ml. Nonspecific antifungals generally have MICs above 100 µg/ml. Some of these can be significantly higher; for example, Leyden & Kligman indicate that the MIC of aluminum chloride against *T. mentagrophytes* is between 100,000 and 200,000 µg/ml (specifically, in Table 1, the authors indicate that 10% aluminum chloride, equal to 100,000 µg/ml, demonstrated no inhibition of *T. mentagrophytes* in an in vitro MIC test, whereas 20% aluminum chloride, equal to 200,000 µg/ml, inhibited the fungus, indicating that the compound's MIC falls somewhere in the range between these two values). Because these concentrations cannot be achieved in the stratum corneum, any activity of these compounds against dermatophytoses relies on a different mechanism, like chemical removal of skin tissue, rather than specifically inhibiting fungal growth.

Early topical treatments for fungal infections were non-specific agents. Rather than inhibiting or killing fungi in particular, they worked primarily by physically or chemically removing the tissue containing the fungi (Gupta, Drugs, Vol. 55, p. 645, 1998). These treatments were minimally effective, due to their inability to target fungi without harming the rest of the skin. Examples of nonspecific antifungals include Whitfield's ointment, Castellani's paint, and aluminum chloride. As treatments specifically targeting fungi were developed, which were significantly more effective and less caustic, these nonspecific antifungal, fell out of favor.

Most common specific antifungal agents function by interfering with ergosterol, a vital component of fungal cell membranes. Polyenes, the first drugs developed to treat fungal infections, bind directly with ergosterol, forming channels through which small molecules are able to leak out of the cell, leading to cellular death. Drugs that belong to this class include amphotericin B, nystatin, hamycin, hachimycin, and natamycin. The drawback of polyenes is their toxicity: they tend to bind to other sterols, including cholesterol in humans. Today, they are used mostly as topical treatments against Candida species.

Azole antifungals, the first specific antifungals to achieve widespread success, work by bonding to the enzyme lanosterol 14α-demethylase, which is essential in converting lanosterol into ergosterol. The fungal cells, unable to produce ergosterol, are unable to remain intact and reproduce, and are shed from the skin. This is a fungistatic mechanism, meaning that fungal growth is impeded but fungi are not immediately killed, and instead patients must wait for the skin to shed its infected stratum corneum. This means that treatment with azoles typically requires longer treatment regimens (four weeks, in many cases) and strict adherence. Well-known azoles include clotrimazole, ketoconazole, fluconazole, flutrimazole, itraconazole, bifonazole, butoconazole, econazole, fenticonazole, isoconazole, luliconazole, miconazole, omoconazole, oxiconazole, ravuconazole, sertaconazole, sulconazole, tioconazole, tiabendazole, vibunazole croconazole, chlormidazole, neticonazole, terconazole, posaconazole, voriconazole, albaconazole, isavuconazole, eberconazole, and efinaconazole. Certain azoles are less effective against the *Trichophyton* species responsible for most cases of tinea pedis and related. dermatophytoses. For example, fluconazole is more effective against *Candida* species than *Trichophyton* species, and thiabendazole is more commonly used as an antiparasitic. However, in certain situations these may be useful in treating dermatophytoses. Recently developed azoles, including luliconazole, lanoconazole, efinaconazole, and sertaconazole, have shown very potent antifungal activity and may be more effective than older azoles; however, more examination of these azoles is required to prove their safety and improved efficacy. The most preferred azoles (those with a particularly useful action spectrum and well-established safety data) include albaconazole, bifonazole, butoconazole, chlormidazole, clotrimazole, croconazole, eberconazole, econazole, fenticonazole, flutrimazole, isavuconazole, isoconazole, itraconazole, ketoconazole, miconazole, neticonazole, omoconazole, oxiconazole, posaconazole, ravuconazole, sulconazole, terconazole, tioconazole, vibunazole, and voriconazole.

Unlike fungistatic azoles, allylamine specific antifungals are primarily fungicidal. These compounds inhibit a different enzyme, squalene epoxidase, which is an essential part of an earlier stage of ergosterol biosynthesis. Like azoles, this leads to ergosterol deficiency; however, allylamines also lead to a toxic accumulation of squalene in the cell, causing more rapid cell death. The fungicidal action of allylamines allows for shorter and more effective therapies: they can be effective even in a single dose, and are less likely to see a relapse after a short course of therapy. Allylamines administered topically include butenafine, naftifine, and terbinafine. Available since the 1990s, terbinafine has become the drug of choice in most cases of tinea pedis, in large part because its shorter treatment regimen leads to increased compliance rates. Preferred embodiments of the invention use fungicides, and allylamines in particular. Terbinafine has been found to be particularly effective.

Tolnaftate is a synthetic thiocarbamate with a specific action spectrum used frequently to treat tinea pedis. Other thiocarbamates include tolciclate and liranaftate. Its exact mechanism of action is not entirely known, but it is believed that tolnaftate interferes with the function of squalene epoxidase, much like allylamines.

Other chemical agents are used as specific and nonspecific antifungals, including amorolfine, clioquinol, nystatin, natamycin, hachimycin, pecilocin, mepartricin, pyrrolnitrin, griseofulvin, bromochlorosalicylanilide, methylrosaniline, tribromometacresol, undecylenic acid, polynoxylin, 2-(4-chlorophenoxy)-ethanol, chlorphenesin, ticlatone, sulbentine, ethyl para-hydroxybenzoate, haloprogin, selenium sulfide, ciclopirox, dimazole, flucytosine, benzalkonium chloride, benzoyl peroxide, benzoic acid, salicylic acid, tannic acid, boric acid, gentian violet, chlorhexidine, cetylpyridinium chloride, tolciclate, sodium thiosulfate, and potassium iodide. Of these, amorolfine, clioquinol, nystatin, natamycin, hachimycin, pyrrolnitrin, griseofulvin, haloprogin, ciclopirox, and tolciclate are specific antifungals useful in the treatment of tinea pedis and related dermatophytoses. More preferred agents include amorolfine, ciclopirox, and tolciclate, whose efficacy is similar to that of azole specific antifungals. Natural remedies are also used as nonspecific antifungals, such as tea tree oil, citronella oil, lemongrass oil, garlic, and vinegar. These are largely ineffective in the treatment of dermatophytoses.

Finally, new specific agents such as tavaborole, abafungin, echinocandins (including caspofungin, cilofungin, micafungin, and anidulafungin), new azoles (including luliconazole, lanoconazole, efinaconazole, and sertaconazole), nikkomycins, pradimicins, and benanomycins may prove to be useful in the treatment of fungal infections, including tinea pedis. Of these, the new azoles (luliconazole, lanoconazole, efinaconazole, and sertaconazole), the echinocandins (anidulafungin, caspofungin, cilofungin, micafungin), and tavaborole have convincingly demonstrated their efficacy and safety in the treatment of dermatophytoses.

Embodiments of the invention can include any of the specific antifungal components listed above. The preferred embodiment utilizes terbinafine, the most effective specific antifungal currently available. The specific antifungal should be present in the invention in a concentration sufficient to treat the dermatophytic infection; as a benchmark, the concentration of the specific antifungal in the stratum corneum 24 hours after application should be above its minimum inhibitory concentration against Trichophyton fungi. For most specific antifungals, the concentration should be between 0.5% and 10%. In most formulations, the concentration of the antifungal will be between 1% and 2%.

Anti-Sweating Agent: Antiperspirant Component

The most common form of anti-sweating agent is the antiperspirant active. All compounds approved by the FDA for use in over-the-counter antiperspirants are aluminum salts, sharing a common mechanism for sweat reduction. Aluminum salts function by obstructing the distal sweat gland duct. They complex with sweat duct keratin and mucopolysaccharides, damaging the sweat duct cuboidal cell lining and forming a polymeric gelatinous cast, which obstructs sweat passage. Sweat production is not shut off; rather the sweat gland, which resides in the reticular dermis and adipose tissues, continues to produce sweat, although the production is greatly reduced due to obstruction of the normal egress route via the aluminum salt complex within the distal sweat duct. It has been noted that the aluminum salt plug may extend down into the secretory coils within the adipose tissue. With long-term aluminum antiperspirant application, secretory cells within the sweat gland are often damaged, with resulting decreased sweat production. Sweat production eventually returns as the cast eventually breaks down. Antiperspirant actives should be distinguished from absorbent agents, such as talcum powder, which function by absorbing sweat after it, has reached the skin's surface. Antiperspirant actives' ability to stop sweat from reaching the skin's surface is vital in this application, where keeping the stratum corneum dry is of great importance.

In some embodiments of the invention, the antiperspirant component can be aluminum chloride, aluminum chlorohydrate, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichlorohydrate, aluminum sesquichlorohydrex polyethylene glycol complex, aluminum sesquichlorohydrex propylene glycol complex, aluminum sulfate buffered, aluminum zirconium octachiorohydrate, aluminum zirconium octachlorohydrex glycine complex, aluminum zirconium pentachlorohydrate, aluminum zirconium pentachlorohydrex glycine complex, aluminum zirconium tetrachlorohydrate, aluminum zirconium tetrachlorohydrex glycine complex, aluminum zirconium trichlorohydrate, or aluminum zirconium trichlorohydrex glycine complex. In general, antiperspirant actives in embodiments of this invention comprise one or more of an aluminum halide, an aluminum chlorohydrate, an aluminum hydroxyhalide, a zirconyl oxyhalide, a zirconyl hyroxyhalide, a zinc halide, an aluminum-zirconium salt, or complexes or adducts thereof with glycols (such as propylene glycol) or neutral amino acids (such as glycine).

Non-aluminum antiperspirants are also commercially desirable due to public concern over the health effects of aluminum intake, although they are often less effective antiperspirants than aluminum salts. Examples of non-aluminum antiperspirants include peptides, methenamine, tannins, and other astringent agents, as well as titanium salts. This invention focuses on aluminum-based antiperspirants due to their proven track record of efficacy and the current scientific understanding that aluminum-based antiperspirants are not linked to an increased risk of cancer or other negative health effects.

In a preferred embodiment, the antiperspirant is aluminum chloride hexahydrate ($AlCl_3 \cdot 6H_2O$), the hydrated form of aluminum chloride. Aluminum chloride hexahydrate is typically used in concentrations of 10-30% in water, aqueous alcohol, or anhydrous alcohol. Higher concentrations are more irritating to the skin. Aluminum chloride hexahydrate also possesses astringent and antimicrobial properties that can be useful in the composition of the present invention.

Anti-Sweating Agent: Other Components

New topical treatments for hyperhidrosis show promise in reducing sweating. One such treatment is anticholinergic agents, which work by competitively inhibiting the neurotransmitter acetylcholine, which regulates sweat production, at receptors on the sweat gland. Previously, anticholinergics were administered systemically, causing significant side effects, but recently the anticholinergic glycopyrronium tosylate has been approved for topical use against hyperhidrosis. This is a promising new treatment because it offers an effective topical anti-sweating agent for those with concern about aluminum intake; furthermore, because the mechanism of action differs from that of antiperspirant actives, the two treatments could be combined to synergistic effect in cases of severe hyperhidrosis. Topical anticholinergic agents are used as anti-sweating agents in some embodiments of the invention; in a preferred embodiment, the anticholinergic is topical glycopyrronium tosylate.

Another class of effective anti-sweating agent is neuromodulators. The most commonly employed neuromodulator is onabotulinumtoxin A (BTX-A), a neurotoxic protein produced by the *Clostridium botulinum* bacterium. Unlike anticholinergic agents, which compete with acetylcholine at receptors, neuromodulators like BTX-A prevent release of acetylcholine altogether. It has been shown to have a powerful and lasting effect against hyperhidrosis; however, it is currently available only in injectable form, which can be painful and inconvenient. Because BTX-A molecules are large, they are unable to cross through the skin barrier in sufficient quantity. However, new research into peptide transport has demonstrated the possibility of BTX-A as a topically applied treatment. As research and development continues, topical neuromodulators such as BTX-A will be potent anti-sweating agents in this invention.

Excipient Component

Excipients include all inactive ingredients added to a pharmaceutical composition. The FDA defines active ingredient as "any component that provides pharmacological activity or other direct effect in the diagnosis, cure, mitigation, treatment, or prevention of disease, or to affect the structure or any function of the body of man or animals;" any element that does not possess this activity is considered an inactive ingredient. In the case of this invention, the specific antifungal and anti-sweating agents are pharmaceutically active ingredients. Alongside these, a variety of excipients may be added to improve the topical application or aesthetic qualities of the composition. Some excipients are vehicles, which assist with the delivery of the composition to the skin; in some embodiments, the terms vehicle and excipient are used interchangeably. Excipients suitable for use with the invention include but are not limited to solvents, solid or semisolid carriers, diluents, bulking agents, propellants, foaming agents, film-forming agents, emollients, humectants, thickening agents, delivery enhancers, surfactants, buffering agents, stabilizers, preservatives, absorbents, anti-static agents, fragrances, and colorants. Individual excipients may fit in one or more of the above-mentioned categories.

Excipients: Vehicles

In the compositions that include a solution (such as a saturated wipe, spray, film-forming solution, or roll-on), the solvent vehicle is used to deliver the active ingredients (antifungal and antiperspirant) to the skin. The solvent vehicle can be selected to enhance or complement the qualities of the active ingredients. The solvent or combination of solvents should be chosen with solubility of the active ingredients and other excipients in mind, to ensure successful dissolution. Exemplary solvents include water, propylene glycol, hexylene glycol, propylene carbonate, benzyl alcohol, and ethanol. In this invention, alcohol-based vehicles are preferred. Alcohols dry quickly, leaving behind no residue, which has aesthetic benefits and contributes to the dryness of the skin. Of particular interest is ethanol (ethyl alcohol), which is discussed in more detail, infra.

In some solid and semisolid compositions (such as stick, gel, cream, foam, lotion, powder, or ointment), solid or semisolid carriers are used as vehicles. Their function is similar to solvents, but they serve as dispersion media in mixtures that are not solutions, such as colloids and suspensions, forming the structure of the compositions. The solid or semisolid carrier may be chosen for additional beneficial qualities, such as improving the application of the composition or soothing the skin. They may also serve as diluents or bulking agents, ensuring topical compositions of the invention do not deliver unsafe or irritating amounts of active ingredients. Exemplary solid or semisolid carriers include silicone-based compounds (such as cyclopentasiloxane), alginic acid, carnauba wax, carrageenan, carbomer, cetearyl alcohol, cetyl alcohol, cetyl ester wax, colloidal silicon dioxide, corn starch, dimethyl sulfoxide, emulsifying wax, fumed silica, gelatin, guar gum, hydrogenated castor oil, hydrous lanolin, hydroxypropyl cellulose, hydroxypropyl methylcellulose, isopropyl myristate, lanolin, lanolin alcohols, magnesium stearate, methylcellulose, microcrystalline wax, mineral oil, octyldodecanol, oleyl alcohol, palm oil, paraffin, petrolatum, polyethylene glycol, polyethylene oxide, sodium carboxylmethylcellulose, soybean oil, stearic acid, stearyl alcohol, sodium alginate, talc, white wax, and yellow wax. Silicone-based compounds such as cyclopentasiloxane are preferred for their comfort in topical solid and semisolid compositions. If the vehicle contains a mixture of oil-based and water-based ingredients, other excipients such as emulsifiers and thickening agents may be required.

Preferred Excipient Vehicle: Ethanol

In some embodiments of the invention, ethanol is a preferred excipient, serving as a solvent vehicle. Ethanol possesses several beneficial properties that can be useful in the composition of the present invention including antimicrobial activity, percutaneous penetration enhancement, and quick evaporation. Ethanol is a well-known antimicrobial, widely used for skin disinfection. Additionally, ethanol tends to dehydrate the skin, which can create an environment inimical to fungal growth. In certain embodiments of the invention, the amount of ethanol in the solvent vehicle may be limited to prevent overdrying of the skin, which may lead to irritation. Ethanol is also advantageous in that it evaporates quickly, which makes it more pleasant than other dermatological vehicles that dry slowly or leave residue behind. Even though ethanol has a tendency to produce a burning sensation, familiar to those who have used rubbing alcohol on a cut or aftershave after shaving, its benefits outweigh this drawback.

Studies that have used ethanol-based vehicles for tinea pedis have reported minimal complaint about burning sensation from patients. Ethanol lowers the threshold temperature at which the transient receptor potential vanilloid 1 (TRPV1) cation channel sends a signal to the brain indicating excessive heat from approximately 42° C. to 34° C. This new threshold temperature is below the core body temperature of 37° C., so normal body temperature causes TRPV1 to produce a burning sensation. However, the average foot temperature is between 30° C. and 34° C., so the burning sensation experienced from ethanol application to the foot is minimal.

Studies have shown that ethanol can enhance percutaneous penetration. In vivo studies indicate that percutaneous terbinafine absorption is enhanced in ethanol solution compared to isopropyl myristate solution (Alberti et al., International Journal of Pharmaceutics, Vol. 21.9, p. 11, 2001). Furthermore, ethanol gel has been shown to improve terbinafine's rate of absorption, maximum concentration, and half-life in the skin compared to a standard cream formulation (James et al., Journal of Dermatological Treatment, Vol. 18, p. 163, 2007). This enhancement allows for decreased treatment frequency and/or duration of therapy compared to cream.

Other Excipients

Along with excipients forming a vehicle, various compositions can include additional excipient components to enhance different qualities of the invention. The addition of a stabilizer or preservative can improve the invention's stability. Similarly, solvents like water and propylene glycol and surfactants can help the solution remain well dispersed. Fragrances can improve the aesthetic qualities of the invention. Other ingredients could be added to the vehicle to slow the release of active ingredients, allowing for less frequent application, or to increase the penetration of the active ingredients.

Propellants are used in aerosol compositions (such as aerosol spray or aerosol foam). They are compounds chosen such that they are liquefied at the pressure inside the aerosol container, but become gaseous once the valve is opened, expelling the composition from the container. Their liquefied state allows a greater amount of the composition to be stored at a lower pressure than compressed-gas aerosol would allow. Exemplary propellants include butane, isobutane, propane, isopropane, dimethyl ether, methyl ether, diethyl ether, methylethyl ether, a hydrofluoroalkane, or a hydrofluoroolefin.

Foaming agents may be used in aerosol or non-aerosol foam compositions. Some foaming agents are surfactants, decreasing the surface tension of the liquid phase and preventing coalescence of the bubbles. Exemplary surfactant foaming agents include sodium lauryl ether sulfate, sodium lauryl sulfate sodium dodecyl sulfate, and sodium coceth sulfate, related compounds, and mixtures thereof. Foaming agents may further comprise propellants (described above) or foam boosters to promote the formation of bubbles. Examples of foam boosters include cocoamidopropyl betaine, cocamidopropylamine oxide, sodium lauroyl sarcosinate, cetearyl alcohol, lauramine oxide, laureth-2, laureth-4, macrocrystalline cellulose, PEG-150 distearate, PVP, and combinations thereof.

Film-forming agents may be added to compositions where the desired effect is a film remaining on the skin for some time after application. This can ensure delivery of active ingredients over an extended period of time, and may allow for effective treatment with less frequent application of the composition, including one-time applications. Exemplary film-forming agents include acrylate polymers, acrylate copolymers, alkyl olefinic acid, alkyl olefinic acid ester copolymers, amide/olefinic acid, amide/olefinic acid copolymers, polyvinyl acetate, polyvinylpyrrolidone, vinylpyrrolidone-vinylacetate copolymer, hydroxyalkyl cellulose, and alkyl cellulose.

Emollients (including silicones, oils, alcohols, and petrolatum) and humectants (including glycerin, propylene glycol, polyethylene glycol, sorbitol, 1,2,6 hexanetriol, sugars, proteins, amino acids, elastin, collagen) are used as moisturizing elements. They can be used to improve experiential qualities, condition the skin, and decrease the risk of overdrying; however, these ingredients must be judiciously selected to avoid counteracting the intended drying effect of the invention. The counterproductive moisturizing effect of the excipients in many cream-based vehicles may be partly to blame for the failure of previous antiperspirant treatments for tinea pedis, including the study on clotrimazole-aluminum chlorohydrate combination therapy conducted by Koca et al. Several problems have been identified with the treatment used in this study. Since patients were subject to twice-daily application, the moisturizing cream vehicle used by Koca inhibited the crucial drying effect of the antiperspirant. Additionally, the specific antifungal and antiperspirant used were less effective against tinea pedis than other antifungals and antiperspirants. This study is yet another reason antiperspirant treatment of tinea pedis has previously been determined to not be effective for tinea pedis. Indeed, in the systematic review of topical treatments for tinea pedis by Crawford & Hollis, the Koca study was excluded even from consideration because the experimental agent included an antiperspirant.

Thickening agents serve to control the texture and viscosity of various compositions. This is especially important in compositions such as gels where the composition is spread or rubbed onto the skin. In such cases, these excipients help ensure that the composition can hold together when picked up with the hands and still spread easily when applied to the skin. Exemplary thickening agents include alginic acid, aluminum starch octenylsuccinate, calcium chloride, carbomer, carrageenan, castor oil, colloidal silicon dioxide, corn starch, cyclomethicone, gelatin, guar gum, hydroxypropyl cellulose, hydroxypropyl methylcellulose, methylcellulose, polyethylene oxide, propylene glycol, silica, sodium alginate, sodium carbyl methylcellulose, sodium starch octenylsuccinate, and stearyl alcohol.

Delivery enhancers may be employed to improve the delivery of active ingredients in a composition. This is especially relevant with active ingredients (such as specific antifungal agents and certain anti-sweating agents) that must penetrate the skin barrier to have their desired effect. As previously discussed, ethanol is a well-known delivery enhancer, assisting with delivery of active ingredients including specific antifungal agents through the skin. Another example is the peptide transport system being developed to enable greater penetration of large BTX-A molecules, an anti-sweating agent, through the skin. Other exemplary delivery enhancers include alcohols (such as benzyl alcohol and isopropyl alcohol), atone, esters (such as ethyl acetate, isopropyl myristate, octyl salicylate, oleyl acetate, and propylene glycol monocaprylate), fatty acids (such as oleic acid), glycols (such as polyethylene glycol and propylene glycol), sulfoxides (such as dimethyl sulfoxide), terpenes, urea, and vitamin E.

Surfactants are substances that reduce the surface tension of liquids, increasing their ability to be dispersed in another substance. One class of surfactants, emulsifiers, are particularly useful in certain compositions, such as creams or gels, where the active ingredients may not be naturally soluble in the vehicle, or the vehicle contains excipients that are not mutually soluble. In these cases, emulsifiers can be used to ensure that the active ingredients will remain well-dispersed throughout the emulsion rather than settling towards separate phases. Surfactants may also be useful as detergents, wetting agents, or foaming agents. Exemplary surfactants include castor oil, diethylene glycol monoethyl ether, docusate sodium, emulsifying wax, glyceryl monostearate, poloxamer, polyethylene glycol distearate, polysorbates, propylene glycol monostearate, sorbitan monostearate, sorbitan monooleate, sodium lauryl sulfate, and stearyl alcohol.

Buffering agents are used in some compositions to ensure the composition is not too acidic or too basic. This is of particular concern in some compositions employing antiperspirants, because these compounds may be very acidic, causing irritation and damage to clothing. A basic buffering agent can help to counteract this acidity. Exemplary buffering agents include citric acid, monosodium phosphate, phosphoric acid, sodium bicarbonate, sodium citrate, sodium hydroxide, and triethanolamine.

Further excipients may be employed in various compositions to ensure the stability of the compositions over time. Preservatives are used to inhibit microbial growth in a composition prior to application. These compounds may have minimal antifungal properties, but they do not reach an in vivo concentration sufficient to have any pharmaceutical effect. Exemplary preservatives include benzalkonium chloride, benzoic acid, benzyl alcohol, chlorobutanol, imidurea, methylparaben, phenoxyethanol, phenyl mercuric acetate, potassium sorbate, propylparaben, sodium benzoate, and sorbic acid. Absorbents (referred to as anti-caking agents in some compositions) help absorb ambient humidity, preventing it from harming the composition. Exemplary absorbents include aluminum starch octenylsuccinate, corn starch, and silica.

Other excipients may be used to improve aesthetic qualities of various compositions. Fragrances may be employed to improve the smell of the composition. Fragrances may be composed of aroma compounds as well as odorless carrier compounds. Exemplary fragrances include botanical extracts, essential oils, esters, and terpenes. Exemplary fragrance carriers include benzyl alcohol, dipropylene glycol, and water. Colorants may be used in certain compositions to change the color of the composition. Acceptable colorants are those approved the FDA for use in foods, drugs, and cosmetics.

The lists of excipients provided here are not comprehensive; further excipients in each class and further classes of excipients may be employed in various compositions to improve their tolerability or desirability. All excipients must be pharmaceutically inactive ingredients.

Form of the composition and its application

The active ingredients (namely, the antifungal and the antiperspirant/anti-sweating agent) and the various excipients and vehicles can be delivered to the skin in a variety of different forms. Example compositions of the invention include liquid solution, spray (aerosol or non-aerosol), foam (aerosol or non-aerosol), solid stick, gel, film-forming solution/mixture, ointment, liquid bath, powder, lotion, and cream. Preferred embodiments of the invention include or use ethanol as a solvent vehicle. Ethanol is preferred over oil- and water-based cream formulations due to its increased drying activity. Liquid forms can be applied by wiping or rubbing on the appropriate body part, such as the feet, or by bathing the body part in the solution. Spray can be sprayed directly onto the skin. The solid stick can be applied using a rubbing motion on the skin. The powder can be sprinkled into a pair of shoes before putting them on or sprinkled directly onto the skin. Additionally, the compound can be incorporated into articles of clothing during manufacture. In all cases, the invention should be applied so that the active ingredients reach the affected area. In some embodiments, the invention is to be applied to the bottom and sides of both feet. Studies have shown that this technique is effective at preventing reinfection, as fungi may have imperceptibly infected other parts of the foot, and are later transferred back to the region of the original infection when not treated. It is contemplated that the compositions of the present invention can be applied to the foot at room temperature. The compositions should be applied to clean and dry feet. In one embodiment the composition is applied before bed.

Active ingredient concentrations can be chosen to deliver the most effective treatment with the best safety profile. The antifungal component can be used in a concentration of about 0.1% to 20%, i.e., 1 to 200 gm/liter of solution. Preferred embodiments have not more than 10% terbinafine. The antiperspirant can be used in a concentration of about 0.1% to about 30% of AlCl3, i.e., not more than about 300 gm of AlCl3 per liter of solution. In the preferred embodiment, the antifungal (terbinafine) is present at a concentration of about 1%, the antiperspirant (aluminum chloride hexahydrate) is present at a concentration of about 15-20%. The compositions of the present invention can be adjusted to treat other microbial infections where moisture due to sweat is a contributing factor, such as bacterial and fungal infections of the foot, armpit, or groin.

A significant advantage of this invention over existing treatments for dermatophytosis is reduced treatment frequency. One of the primary causes of treatment failure with existing treatments is poor adherence. Patients discontinue treatment before the fungus is successfully eradicated because twice-daily application of an oily cream is inconvenient and unpleasant. Because of the synergistic effects of the combination therapy, which mates the active ingredient more effective than either would be on its own, less frequent treatment is possible. Once-daily application is the standard regime for this invention, but even less frequent treatment may be possible. Patients are more likely to adhere to a less burdensome treatment schedule, so there is a greater likelihood that the fungus will be successfully eradicated with this invention.

Wipe Embodiment

Embodiments of the invention use disposable wipes to apply the composition to the affected area of the skin, a novel delivery mechanism in the treatment of tinea pedis. This new topical application represents a significant step forward in the treatment of tinea pedis, where a large proportion of treatment failures are due to patient non-compliance rather than non-efficacy of treatment (de Chauvin et al., Mycoses, Vol. 51, p. 1, 2007). The wipe embodiment offers benefits in terms of dosing assistance, cleaning, and convenience.

Materials & Manufacture

In a preferred embodiment, wipes are a disposable non-woven polyester-viscose blend, which is more absorbent than polyester alone. Any combination of man-made and/or natural fibers could be used, with the caveat that it may be necessary to adjust the formulation or volume of solution to ensure proper delivery of active ingredients. For example, a less-absorbent 100% polyester wipe may need to be saturated with a more concentrated solution to deliver the proper dose of active ingredients. Pharmacokinetic testing can be used to ensure that an appropriate dose of active ingredients is successfully deposited on the skin.

The untreated wipes can be folded and inserted into individual pouches (which are sealed on three sides and open on one side). The pouches can be metal-laminated polyethylene with a notch at the side to enable easy tearing. Other individual pouch materials, including foil-laminated paper or un-laminated polyethylene, are possible. Alternatively, the wipes may be packaged in a resealable container rather than individual pouches. In this case, the solution will need to be formulated to ensure that all wipes remain properly saturated.

The liquid solution, which contains the active ingredients, is added to the pouch, and the pouch is sealed on its open side. If necessary, pressure can be applied to the pouch to assure adequate saturation throughout the wipe. The packaging process can be accomplished by a packaging machine, or can be done by hand when small quantities are required.

Application

To use the wipe, the end of the package should be torn off to open it, the wipe should be unfolded, and patients should wipe any affected areas by hand. In the case of interdigital tinea pedis, patients should thoroughly wipe each interdigital space. In some embodiments, the bottom and sides of both feet should be wiped. Studies have indicated that this technique is effective at preventing reinfection, as fungi may have imperceptibly infected other parts of the foot, and are later transferred back to the region of the original infection when not treated. Wipes can be packaged with two wipes in a pouch, one for each foot, or one wipe can be used for both feet, as long as the saturation is appropriate for the application.

Benefits of the Wipe Embodiment

Dosing Assistance

In some embodiments, the disposable wipe application. provides a greater degree of control over patient dosing, as compared with creams, gels, or sprays. Unlike conventional topical treatments, where patients may use too little (resulting in insufficient drug delivery) or too much (causing their supply of treatment to run out before the end of therapy), an individually packaged wipe provides a correct dose of active ingredients with less possibility for error. Current approaches to tinea pedis treatment often fail due to premature discontinuation of therapy by patients, who may stop using topical treatments once their symptoms have resolved but before the infection is fully eliminated. The compositions using the wipe invention can be packaged in discrete quantities (for example, 28 individual packets for a 4-week course of treatment) rather than one tube with an indeterminate number of doses; thus, patients may be more likely to adhere to a full treatment regime. Embodiments of the invention include packages that have 7 or 14 packets (e.g., wipes), anticipating treatment durations for one or two weeks. Daily administrations are preferred, to minimize overdrying while simultaneously providing the required therapeutic value. Such administrations, which include the antifungal, antiperspirant, and the drying agent, have been found to be therapeutically effective regardless of the stage of the disease at the time treatment is commenced.

Disposable wipes can also assist with pulse therapies. For example, in a four-week antifungal-antiperspirant combination therapy, it could be beneficial to reduce the application of antiperspirant to twice weekly while still applying the antifungal every day. Rather than asking patients to keep track of what drugs to apply on which days, they could be offered 28 individual pouches with the appropriate drugs for each day, labeled with the day of intended use. This enables the patients to conveniently apply the correct medication, and increases the likelihood of adhering to a full course of therapy.

Cleaning Effect

The disposable wipe application takes advantage of friction, an important component of cleansing any surface. Patients tend to apply friction more effectively when they do not make direct contact with the skin. This is due in part to the natural lubrication of oils on the skin, and in part to an understandable hesitance to dig deeply into infected areas. Furthermore, the disposable wipe application decreases the risk of accidental manual transmission by providing a barrier between the hand and the infected foot, which decreases the patient's hesitation in applying the medication, increasing the friction applied and thus cleaning the infected skin.

Convenience and Comfort

Many existing topical antifungal applications, especially topical cream, leave an oily residue on the skin. Many patients find this unpleasant, particularly when they need to put socks and shoes on shortly after application. Because the wipe allows for the drug to be delivered in a liquid solution, rather than requiring a semisolid emulsion like a cream or gel, solvents like ethanol can be used in liquid form. Ethanol is a preferred vehicle excipient, because it evaporates quickly, produces a cooling sensation, and leaves the skin dry. This experience, which many patients find pleasant, contributes to ethanol's popularity in other topical products, including hand sanitizes and aftershave. Likewise, by using ethanol the composition does not leave an oily residue on the hands. Furthermore, the tendency of ethanol to cause a burning sensation is minimized when applied to the foot, because the foot's temperature is lower than the rest of the body (see full explanation of ethanol's effect on TRPV1 in the "Preferred Excipient Vehicle: Ethanol" section above).

Patient non-compliance is a significant hurdle in the effective treatment of tinea pedis, and the compositions of the present invention increase patient comfort and thus offer a significant improvement over existing therapies since patient compliance is increased. The simple process of opening the package, wiping the feet, and throwing the wipe away mimics the familiar experience of using a moist towelette on one's hands at a restaurant, and the lack of residue left behind on the hands and feet means that patients will be inclined to continue therapy longer than they otherwise might.

EXAMPLE 1

Exemplary Test Results Using Compositions of the Invention

Initial trials of an embodiment of the invention were conducted with patients suffering from tinea pedis, comparing once-daily application of the invention to the current standard treatment for tinea pedis, twice-daily application of terbinafine cream, as well as a placebo (consisting of a towelette saturated with ethanol, but containing neither an antifungal nor an antiperspirant). Results of the study indicated that once-daily treatment with the invention was similarly effective to twice-daily treatment with terbinafine cream, and significantly more effective than placebo. Thirty

(30) patients were treated with each method for 4 weeks, and results were recorded 2 weeks after the conclusion of treatment. A potassium hydroxide preparation was used to test for the presence of fungi. At the conclusion of the study, 21 patients treated with the invention had negative results, compared to 22 patients treated with terbinafine cream. Only 8 patients treated with placebo were negative at the end of the study. Subjective feedback from patients favored the invention. The cream was described as "slippery" and "uncomfortable," and twice-daily application was described as a "hassle," while the invention was described as "very easy to use" and "very effective." One patient said she would be "ecstatic" to see the invention available commercially, while another, at the study's conclusion, declared that this was the "best condition my feet have ever been in."

Table 1: Negative KOH After 6 Weeks

TABLE 1

Negative KOH After 6 Weeks

| Treatment | Number of Patients with Negative KOH |
|---|---|
| Invention (1×/day) | 21/30 |
| Terbinafine cream (2×/day) | 22/30 |
| Placebo (1×/day) | 7/30 |

These study results indicate that once-daily application of the invention is similarly effective to twice-daily application of terbinafine cream. This increased convenience is particularly salient because poor treatment adherence is a major reason why tinea pedis treatments fail in practice. A treatment that requires less frequent application is more likely to be used for the full treatment period, and thus is more likely to lead to positive outcomes in real-world applications where treatment discontinuation is more likely. The positive response of patients to the treatment also indicates that the treatment would be better received than the current standard treatment. Patients preferred the dry sensation of the invention over the oily cream, and this experiential preference would further improve adherence, and thus outcomes.

This study design was chosen to be in line with standard clinical trials for antifungal treatments for tinea pedis, which use a 4-week course of treatment and require confirmation of fungal infection. As previously discussed, this excludes patients whose fungal infection has been superseded by bacterial infection. For these patients, the invention is likely to be significantly more effective than an antifungal alone.

EXAMPLE 2

Exemplary Method for Manufacturing the Composition

Ethanol is added to a container, with the volume of ethanol not to exceed 75% of the desired final volume. Terbinafine powder is added to the container and stirred. The mass of terbinafine is added such that the concentration of terbinafine will be about 10 grams per liter of the solution at the desired final volume. Crystalline aluminum chloride hexahydrate is added to the solution, such that the concentration will be about 200 grams per liter of aluminum chloride at the desired final volume. The crystalline aluminum chloride hexahydrate may be crushed before addition to enable faster dissolution. Further inactive excipients may be added to improve qualities of the composition. After the excipients, terbinafine, and aluminum chloride hexahydrate have been added to the solution, more ethanol is added until the volume reaches the desired final volume. The container is sealed to prevent evaporation, and the solid ingredients dissolve to create a uniform solution. Heat and agitation may be introduced to expedite the process of dissolution. A wipe can be saturated with the solution for application by a patient.

EXAMPLE 3

Treatment and Cost Savings Using the Invention

In certain embodiments, such as a spray a gel, patients apply the invention directly to the foot. In these cases, the invention has the potential for cost savings over existing treat cent since once-daily treatment with the invention achieves the same efficacy as twice-daily treatment with a standard antifungal. The antiperspirant component added to the invention is less expensive to produce than the additional amount of antifungal that is required in twice-daily treatments. Furthermore, because the invention may be more pleasant and more effective than existing treatments, patients are less likely to discontinue treatment early and experience a relapse of the infection, requiring additional treatment. This kind of redundant retreatment is a significant cost in the treatment of tinea pedis, and is reduced by the invention.

EXAMPLE 4

Consistent Treatment Irrespective of the Stage of the Infection

One advantage of the invention compared to existing treatments for tinea pedis is its ability to treat the infection regardless of the stage of the infection. As previously noted, the simple form of the disease (dermatophytosis simplex is a purely fungal infection, characterized by dry, flaky skin. When bacteria proliferate in the infected space, supplanting the fungi, the disease is called dermatophytosis complex, and is characterized by more unpleasant symptoms, notably maceration and odor. At this stage of the disease, antifungals alone are less effective since bacteria have become the dominant agent in the infection. Lay knowledge of this distinction is not widespread, and both stages of the disease are recognized as "athlete's foot;" thus, it is likely that a person whose infection has progressed to the dermatophytosis complex stage will seek out a common treatment for athlete's foot, such as an over-the-counter topical antifungal cream, which is unlikely to be effective against this stage of the disease. It may take several unsuccessful treatments, an appointment with a dermatologist, and laboratory work to correctly identify and treat the infection.

This invention is advantageous because it is effective against tinea pedis at any stage in its development. The antifungal eliminates fungi, the antiperspirant and the alcoholic vehicle excipient have antibacterial activity, and the sweat-blocking activity of the antiperspirant and the drying effect of the alcohol lead to a dry environment inimical to fungal and bacterial growth. Patients and clinicians thus benefit from having one treatment that is effective against tinea pedis, regardless of the stage of infection, reducing the possibility of ineffective treatment and the need for diagnostic testing to determine the correct treatment.

EXAMPLE 5

Treatment of Various Dermatophytoses

This invention is promising for its ability to treat various forms of dermatophytes. Tinea pedis has been discussed herein at length, but the benefits of an antifungal-antiperspirant combination therapy extend to other dermatophytoses where perspiration can be an exacerbating factor. Tinea cruris (jock itch) affects the groin, which is an ideal environment for fungal growth due to moisture and heat trapped by occlusive clothing. Tinea corporis (ringworm) commonly affects areas where sweat accumulates, such as armpits and abdominal skin folds. Other dermatophytoses, including tinea manuum, are more common among those who sweat excessively. In all of these cases where sweat is a contributing factor to the development and persistence of a fungal infection, antifungal-antiperspirant treatment is advantageous. By reducing sweat, it inhibits conditions favorable to fungal growth, and its activity against a broad spectrum of microorganisms ensures successful treatment of the fungal infection and any opportunistic co-infection that may arise in the weakened stratum corneum.

EXAMPLE 6

Exemplary Patient Adherence with Embodiments of the Invention

Different formulations of the composition have been given to patients experiencing dermatophytosis with highly beneficial results. One patient with chronic tinea pedis was given a solid stick containing 16% aluminum zirconium tetrachlorohydrex gly and 1% tolnaftate, along with various excipients to improve comfort and ease of application. This formulation was successful in resolving the patient's tinea pedis. After the infection had been resolved, the patient continued using the composition until the entire stick was consumed, appreciating the comfort of dry feet provided by the antiperspirant. Similar results were achieved with a second patient, using solid stick containing 16% aluminum zirconium tetrachlorohydrex gly and 1% terbinafine. Because patient adherence is a large obstacle preventing successful treatment, and a particular problem is the patient discontinuing treatment once visible symptoms have improved but before the underlying infection is resolved, a composition with sufficient aesthetic benefits to encourage good adherence represents a significant positive development in the treatment of dermatophytoses.

EXAMPLE 7

Exemplary Composition of the Invention: Solid Stick

The following ingredients may be combined to form a solid composition of the invention, In an appropriate container, this may be rubbed smoothly onto the skin to deliver the composition across the skin surface.

| Ingredient | Exemplary Concentration (% by weight) | Concentration Range (% by weight) |
|---|---|---|
| Zirconium-Aluminum-Glycine Hydroxychloride Complex (Anti-Sweating Agent) | 26.7 | 5.0-30.0 |
| Butenafine (Specific Antifungal) | 2.0 | 0.5-2.0 |
| Cyclomethicone | 48.6 | 35.0-60.0 |
| Stearyl Alcohol | 11.3 | 10.0-15.0 |
| Dimethicone | 3.0 | 1.0-5.0 |
| Castor Wax | 2.9 | 2.5-4.0 |
| Colloidal Silica | 0.5 | 0.2-1.5 |
| Low-Density Polyethylene Powder | 1.0 | 0.5-4.0 |
| Anhydrous Aluminum Silicate Powder | 4.0 | 2.0-9.0 |
| Fragrance | <0.1 | <1.0 |

EXAMPLE 8

Exemplary Composition of the Invention: Aerosol Spray

The following ingredients may be combined in an aerosol canister to form an aerosol spray composition of the invention.

| Ingredient | Exemplary Concentration (% by weight) | Concentration Range (% by weight) |
|---|---|---|
| Aluminum Chlorohydrex Propylene Glycol (Anti-Sweating Agent) | 12.5 | 5.0-30.0 |
| Clotrimazole (Specific Antifungal) | 1.0 | 0.5-2.0 |
| SD Alcohol 40-2 | 21.5 | 15.0-45.0 |
| Propylene Carbonate | 32.3 | 15.0-55.0 |
| isobutane | 6.7 | 1.0-30.0 |
| N-Butane | 2.4 | 1.0-30.0 |
| Propane | 1.0 | 0.5-30.0 |
| Cyclomethicone | 7.4 | 5.0-15.0 |
| Phenyltrimethicone | 6.6 | 5.0-15.0 |
| Isopropyl Palmitate | 8.6 | <10.0 |

EXAMPLE 9

Exemplary Composition of the Invention: Solution

The following ingredients may be combined to form a solution composition of the invention. There are a number of ways to apply such a solution to the skin; the solution could be used with a container to roll or spray the solution onto the skin, or a wipe could be impregnated with this solution, among other options.

| Ingredient | Exemplary Concentration (% by weight) | Concentration Range (% by weight) |
|---|---|---|
| Aluminum Chlorohydroxide Propylene Glycol Complex (Anti-Sweating Agent) | 15.0 | 5.0-30.0 |
| Miconazole (Specific Antifungal) | 1.0 | 0.5-2.0 |
| Ethanol | 69.0 | 40.0-85.0 |
| Stearic Acid | 1.5 | 0.5-5.0 |
| Isopropyl Myristate | 1.0 | <10.0 |
| Volatile Cyclic Polydimethyl Siloxane | 11.0 | 5.0-40.0 |
| Polyphenylmethyl Siloxane | 1.0 | 0.5-5.0 |
| Perfume | 0.5 | <1.0 |

While the invention has been particularly shown and described with reference to specific preferred embodiments, it should be understood by those skilled in the art that various changes in form and detail may be made therein without departing from the spirit and scope of the invention as defined by the following claims.

I claim:

1. An antibiotic-free composition effective in treating a dermatophytic infection, the composition comprising actives selected from a group of antifungals and a group of anti-sweating agents, the antibiotic-free composition comprising:
    an antifungal active from the group of antifungals being 0.5 to 2.0 wt. % of a specific antifungal, the specific antifungal being terbinafine, present in an amount sufficient to effectively treat the dermatophytic infection;
    an anti-sweating active from the group of anti-sweating agents being 5.0 to 30.0 wt. % of an anti-sweating agent, the anti-sweating ageing being aluminum zirconium tetrachlorohydrex gly; and
    one or more excipients for topical application of the composition.

2. The composition of claim 1 wherein the one or more excipients is a liquid and the composition is in the form of a solution.

3. The composition of claim 2 wherein the one or more excipients includes an alcohol.

4. The composition of claim 1 wherein the one or more excipients includes at least one of a solvent, solid or semi-solid carrier, diluent, bulking agent, propellant, foaming agent, film-forming agent, emollient, humectant, thickening agent, delivery enhancer, surfactant, buffering agent, stabilizer, preservative, absorbent, anti-static agent, fragrance, or colorant.

5. A method for antibiotic-free treatment of a dermatophytic infection, comprising the steps of:
    topically applying a specific antifungal, the specific antifungal being terbinafine and present in an amount between 0.5 and 2 wt. %, the specific antifungal sufficient to effectively treat the dermatophytic infection;
    topically applying an anti-sweating compound, the anti-sweating compound being 5.0 to 30.0 wt. % of aluminum zirconium tetrachlorohydrex gly;
    topically applying one or more excipients to assist the topical application, wherein the specific antifungal, the anti-sweating compound and the one or more excipients are all applied during a single administration event, such that an efficacious result can be achieved by only daily administrations.

6. The method of claim 5 wherein the applying is in the form of a solution, a spray or a wipe.

7. The method of claim 5 wherein the applying results in a topical antifungal skin concentration of greater than or equal to the MIC of the antifungal.

8. The method of claim 7 where the topical antifungal skin concentration 24 hours after application is equal to or greater than the MIC of the antifungal.

9. The method of claim 5 wherein a duration of the treatment is between one and four weeks.

10. A composition for treatment of a dermatophytic infection produced by the process of:
    adding a specific antifungal to an excipient to create a mixture, the specific antifungal being 0.5 to 2.0 wt. % terbinafine;
    adding a measured amount of anti-sweating agent to the mixture, the anti-sweating agent being 5.0 to 30.0 wt. % aluminum zirconium tetrachlorohydrex gly;
    adding additional excipient, if required, to establish a concentration of the specific antifungal sufficient to effectively treat the dermatophytic infection; and
    establishing uniform dispersion of the specific antifungal, the anti-sweating agent and the excipient(s) in the mixture by mixing, if necessary.

11. The composition of claim 10 wherein the mixture is distributed on a wipe for treatment of a dermatophytic condition of a patient.

12. The composition of claim 10 wherein the excipient comprises an alcohol.

13. A kit for the treatment of a dermatophytic condition comprising:
    an article, the article comprising:
        an anti-sweating agent that includes 5.0 to 30.0 wt. % aluminum zirconium tetrachlorohydrex gly;
        a specific antifungal of terbinafine present in an amount of between 0.5 and 2.0 wt. %, sufficient to effectively treat the dermatophytic infection,
        one or more excipients for topical application of the composition, and
    a storage container for housing the article.

14. The kit of claim 13, the kit further comprising an applicator, the applicator including at least one of a wipe, push stick, spray or foam nozzle, aerosol container and nozzle, or roller ball.

* * * * *

UNITED STATES PATENT AND TRADEMARK OFFICE
CERTIFICATE OF CORRECTION

| | | |
|---|---|---|
| PATENT NO. | : 11,554,108 B2 | Page 1 of 1 |
| APPLICATION NO. | : 16/378082 | |
| DATED | : January 17, 2023 | |
| INVENTOR(S) | : Carl Schanbacher | |

It is certified that error appears in the above-identified patent and that said Letters Patent is hereby corrected as shown below:

On the Title Page

First Column, the Related U.S. Application Data has been incorrectly listed. It should read as follows:
--(63) Continuation-in-part of application No. 15/683,416, filed on Aug. 22, 2017, now Pat. No. 10,251,822.--

Signed and Sealed this
Third Day of October, 2023

Katherine Kelly Vidal
Director of the United States Patent and Trademark Office